United States Patent [19]

Woods

[11] 4,042,633

[45] Aug. 16, 1977

[54] PROCESS FOR PREPARING DIISOPROPYL ETHER

[75] Inventor: Hanbury John Woods, Campbellville, Canada

[73] Assignee: Gulf Oil Canada Limited, Toronto, Canada

[21] Appl. No.: 693,579

[22] Filed: June 7, 1976

[51] Int. Cl.$^2$ .................. C07C 41/10; C07C 41/06
[52] U.S. Cl. ........................ 260/614 R; 260/614 A
[58] Field of Search ..................... 260/614 R, 614 A

[56] References Cited

U.S. PATENT DOCUMENTS

| | | | |
|---|---|---|---|
| 2,067,385 | 1/1937 | Evans et al. | 260/614 A |
| 2,148,288 | 2/1939 | Bent | 260/614 R |
| 2,282,469 | 5/1942 | Frolich | 260/614 R |
| 2,805,261 | 9/1957 | Keith | 260/614 A |
| 2,845,463 | 7/1958 | Friedman et al. | 260/614 A |
| 3,440,293 | 4/1969 | Russcup et al. | 260/614 A |

FOREIGN PATENT DOCUMENTS

| | | | |
|---|---|---|---|
| 1,249,845 | 9/1967 | Germany | 260/614 A |

OTHER PUBLICATIONS

Evans et al., Ind. & Eng. Chem., vol. 28, No. 10, 1186–1188.
Runge et al., Chem. Abst., 48, 2353i, 1954, Brennstoff Chem. 34, 330–333, 1953.

Primary Examiner—Howard T. Mars
Attorney, Agent, or Firm—D. R. Morrison

[57] ABSTRACT

Diisopropyl ether is prepared from isopropanol in liquid phase in contact with particular Montmorillonite clay catalysts, optionally in the presence of added propylene. The process is operated in a continuous manner by continuously feeding liquid isopropanol, optionally with added propylene, into a reaction space where the feed contacts the catalyst at 120° to 250° C for an average contact time of 1 to 120 minutes. Pressure is maintained in the reactor to keep a liquid phase in contact with the solid catalyst. Effluent withdrawn continuously from the reaction space at the feed rate is separated by fractionation to recover diisopropyl ether.

7 Claims, No Drawings

PROCESS FOR PREPARING DIISOPROPYL ETHER

This invention relates to the preparation of diisopropyl ether. More particularly the invention relates to the preparation of diisopropyl ether in a combination of reactions in contact with particular catalyst which catalyzes the formation of diisopropyl ether simultaneously over different routes.

Diisopropyl ether has long been known as a good blending compound for high octane gasolines. There are numerous processes available for the preparation of diisopropyl ether, most of them generally expensive. A major proportion of commercial diisopropyl ether currently available is produced as a by-product in the manufacture of isopropanol, as commonly produced by the hydration of propylene. In the equilibrium reaction for the hydration of propylene to isopropanol in accordance with the equation:

$$C_3H_6 + H_2O \rightleftharpoons C_3H_7OH \qquad (1)$$

there is also formed some by-product diisopropyl ether by a series of equilibrium reactions whose sum total may be expressed by the equation:

$$2C_3H_6 + H_2O \rightleftharpoons C_3H_7OC_3H_7 \qquad (2)$$

Both these equilibrium processes are acid catalyzed, and both include hydration and dehydration steps.

It is also known that isopropanol can be partially dehydrated to diisopropyl ether, in accordance with the equation:

$$2C_3H_7OH \rightleftharpoons C_3H_7OC_3H_7 + H_2O \qquad (3)$$

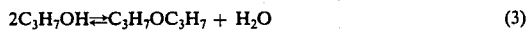

This equilibrium reaction likewise is acid catalyzed. Furthermore, the alcoholysis of propylene by isopropanol to form diisopropyl ether also is possible, in accordance with the equation:

$$C_3H_7OH + C_3H_6 \rightleftharpoons C_3H_7OC_3H_7 \qquad (4)$$

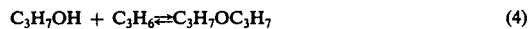

Again the reaction is one which, like the preceding ones, is a reversible one, achieving equilibrium between ingredients on each side of the equation, and likewise it may be acid catalyzed.

It is apparent that combinations of catalyst and conditions most favorable to the hydration steps will not be those which are most favorable to the dehydration steps, and it is unlikely that any combination of catalyst and reaction conditions can be expected simultaneously to promote competing hydration and dehydration steps.

It has now been found that the partial dehydration of isopropanol to diisopropyl ether can be achieved using a particular type of catalyst novel for such reaction and, under appropriate conditions, there can also be achieved, simultaneously with the dehydration, some alcoholysis of propylene to form additional diisopropyl ether.

The invention thus consists in a process for the preparation of diisopropyl ether which comprises continuously feeding isopropanol, and optionally propylene, in the liquid phase under pressure into a reactor in which the feed material comes into effective contact with a solid catalyst, continuously withdrawing a mixture of reaction products and unreacted isopropanol and propylene from the reactor, and recovering diisopropyl ether from the mixture, said solid catalyst comprising acidic, sulfuric acid treated, Montmorillonite clay containing sufficient residual acidity to impart a pH below 4 thereto, said reactor being heated to maintain a maximum temperature in the reactor in the range from substantially 120° C to substantially 250° C. In a preferred embodiment the invention consists of a process for the preparation of diisopropyl ether which comprises continuously feeding isopropanol, and optionally propylene, in the liquid phase under pressure into an elongated (preferably tubular) reactor containing a solid catalyst, continuously withdrawing the resulting mixture of reaction products and unreacted isopropanol and propylene from the reactor at a point remote from the point of introduction of the reactants, and recovering diisopropyl ether from the mixture, said solid catalyst comprising acidic, sulfuric acid treated, Montmorillonite clay containing sufficient residual acidity to impart a pH below 4 thereto, said reactor being heated to maintain a maximum temperature in the reactor in the range from substantially 120° C to substantially 250° C, preferably 175° to 225° C, most preferably 185° to 210° C. Another specific embodiment of the invention consists of a process comprising continuously feeding reactants, isopropanol and optionally propylene as fed to an elongated reactor in the preferred embodiment, but in this case to a simple stirred enclosed reaction space under pressure which maintains catalyst submerged in liquid phase reaction mixture and in continuously changing contact therewith, said catalyst comprising acidic, sulfuric acid treated, Montmorillonite clay containing sufficient residual acidity to impart a pH below 4 thereto, continuously stirring and maintaining a temperature in the range from substantially 120° C to substantially 250° C, and continuously withdrawing reaction mixture from the reaction space at a rate equal to the rate of feed of reactants, then recovering diisopropyl ether from the said effluent.

Inasmuch as the invention permits achievement of optimum yields and production rates for conversion of isopropanol to diisopropyl ether, it can be combined with any other process which can provide optimum yields and production rates for conversion of propylene to isopropanol and thereby provide optimum yield and production rate for the over-all conversion of propylene to diisopropyl ether.

From the foregoing statement of invention it will be appreciated that, with both isopropanol and propylene being fed into a reator containing an acidic catalyst, several reactions can occur. More particularly, initially the reactions set out above in equations (3), (4) and (1) may occur, with reaction (1) occurring in the reverse direction only, unless some water is present in the isopropanol feed or until some water has been formed as the co-product of reaction (3). Unless water is also present in the feed, reaction (2) cannot occur until water is formed in the reaction mixture by the reaction of equation (3) and/or equation (1) in reverse, and unless propylene is present in the feed, reaction (4) cannot occur until propylene is formed in the reaction mixture by reaction (1) in reverse. As soon as some diisopropyl ether is present in the mixture, formed in any of equations (2), (3) and (4), the reactions of equations (2), (3) and (4) in reverse will begin to occur. For any specific set of relative proportions of the ingredients isopropanol, propylene, and water, under any specified conditions of temperature and pressure, a single equilibrium concentration of diisopropyl ether would eventually be achieved in contact with acidic catalyst, regardless of what the acidic catalyst is, inasmuch as any true catalyst affects only the rate of reactions but has no effect on the equilibrium concentrations of reactants and products. The critical feature of the present invention is the use of the specific acidic catalyst disclosed which appears to catalyze the reactions forming diisopropyl ether, viz: the alcoholysis of propylene and the hydration of propylene (i.e., propylene consuming reactions) more rapidly than it catalyzes the reactions yielding propylene, to the extent that there may be a net consumption of propylene from the feed rather than a net production of propylene by the various reactions within the reactions times, i.e., catalyst contact times, appropriate for the commercial production of diisopropyl ether; the reactions yielding propylene in these circumstances are the reaction of equations (1), (2) and (4), all in reverse. No other acidic catalyst has been found which does this as efficiently as that disclosed herein.

The invention is illustrated more specifically in the following examples which also show, for comparative purposes, the net production of propylene when other catalysts are used with the same reactants, in contrast to the consumption of propylene that can occur with use of the catalyst of the present invention.

The examples were carried out in an apparatus which included a stainless steel tubular reactor formed from pressure tubing, 39.3 inches (1 meter) in length and 0.3 inches (7.6 mm) in internal diameter; the tubing was mounted vertically for reactants to flow downwardly therethrough and effluent to be withdrawn at the bottom. The tubing was wrapped with electrical heating tape as was the adjacent section of the pressured feed line to the top of the reactor tube, thereby forming a preheat zone which brought reactants to the desired reaction temperature range. Reactant liquid propylene (when called for) was stored in a reservoir under a blanket of nitrogen and fed by nitrogen pressure to the inlet of a high pressure metering pump. The isopropanol was fed by gravity to the inlet of a second high pressure metering pump. The metering pumps pumped the liquid reactants in the desired proportions to a common feed line containing an appropriate back pressure regulator and a nonreturn valve, through the aforementioned preheated section, and into the reactor. A fine thermocouple well extended into the reactor from the top for one third of the reactor length, permitting the measurement of temperature at any point along that part of the reactor. The effluent line leading from the bottom of the reactor passed through a coller providing indirect heat exchange with cold water, through a second back pressure regulator valve and a non-return valve to a gas chromatograph pressure sample point and by-pass, and thence to a liquid pressure storage vessel. A vent line from this vessel led through a pressure reducing valve and metering valve to a vent at atmospheric pressure. Appropriate weights of catalyst charge were inserted in the reactor tube to achieve desired contact times of reactants flowing therethrough at rates conveniently achieved with the pumping facilities being used. When the amount of catalyst occupied less than the complete volume of the reactor, the bottom part of the reactor was filled with inert glass beads to retain the catalyst in the upper part surrounding the thermocouple well. For catalysts where the active material was in the form of a finely divided powder which would tend to pack and clog the passage through the reactor, the powder was mixed with, and held dispersed in, an inert carrier, specifically in the following examples, inert medium fibre asbestos in a convenient weight ratio of 70:30 powder:asbestos, to provide a catalyst that remainded porous to the flow of liquid reaction mixture when packed to a convenient bulk density in the reactor. From the weight of catalyst, bulk density, and pumping rates of reactants, the liquid hourly space velocites of reactants (reciprocal contact times) were calculated.

EXAMPLE 1

This first example illustrates the preparation of diisopropyl ether by dehydration of isopropanol in a series of runs in the aforementioned apparatus, each run using a different catalyst or temperature and all under essentially the same uniform operating conditions of 1600 psig (110 atm.) pressure, specified temperature, and continuous uniform reactant flow rate to provide a liquid hourly space velocity (LHSV) of substantially 10. (The LHSV was calculated as the total liquid volume of reactants entering the reactor hourly, measured at room temperature, divided by the volume of the part of the reactor occupied by the catalyst bed.) The different catalysts were mixtures of various activated Montmorillonite clays in fine powder form dispersed on inert acid washed medium fibre asbestos carrier in a weight ratio of active ingredient/carrier of 70/30. This dispersion of the active powder ingredient was adopted to provide porosity and preclude packing of the powder and blockage of the flow of liquid through the catalyst bed. The specific clays in the catalysts, herein designated as Catalysts I, II, III and IV respectively, were commercial, powdery, sulfuric acid activated, Montmorillonite clay products sold under the tradenames and having the significant properties as shown in Table I.

TABLE I

| Catalyst | I | II | III | IV |
|---|---|---|---|---|
| Tradename | KSF | K-10/SF | KSF/0 | K-10 |
| pH Value* | 2.1 | 2.4 | 2.4 | 3.6 |
| Surface (m²/g) | 18 | 108 | 189 | 268 |
| Bulk Density (g/l) | 809 | 380 | 351 | 373 |
| Specific Gravity | 2.4–2.5 | 2.4–2.5 | 2.4–2.5 | 2.4–2.5 |
| Proximate Analysis (%) | | | | |
| $SiO_2$ | 53.2 | 58 | 69.8 | 64.7 |
| $Al_2O_3$ | 18.8 | 16 | 14.2 | 19.3 |
| $Fe_2O_3$ | 5.1 | 5 | 3.2 | 5.1 |
| CaO | 2.9 | 1 | 0.8 | 0.9 |
| MgO | 2.8 | 3 | 0.9 | 2.8 |
| Loss on Ignition | 8.1 | 6 | 6.1 | 7.2 |
| $H_2SO_4$ | 6 | 5 | 5 | — |

*pH measured on 100 ml distilled water into which 8 grams of the clay powder is dispersed. All references to pH of Montmorillonite clay in this specification and claims are intended for measurement in this manner.

In the series of runs, each catalyst was used at several specific different temperatures indicated in the following Table II. Periodic analysis, during each run, of samples of the reactor effluent, using a gas chromatograph, established the weight percent of each component in the effluent (diisopropyl ether, isopropanol, water, and propylene). From the analyses, the percent conversion of isopropanol (IPA Conversion, %) was calculated and is reported hereunder in Table II for each run, together with the calculated selectivity of the conversion to diisopropyl ether, expressed as a percent of the total conversion (Selectivity, %), and the rate of production of diisopropyl ether calculated in gram mols per hour per gram of catalyst (active ingredient only) in the reactor (DIPE Prodn, gM/hr/g Cat.).

TABLE II

| Catalyst | Reaction Temp (° C) | IPA Conversion (%) | Selectivity DIPE Prodn (%) | (gM/hr/g Cat.) |
|---|---|---|---|---|
| I | 175 | 41.0 | 68.0 | .0533 |
| " | 185 | 44.6 | 67.7 | .0577 |
| " | 200 | 55.9 | 58.9 | .0630 |
| " | 215 | 63.0 | 50.9 | .0613 |
| II | 175 | 20.9 | 68.9 | .0297 |
| " | 185 | 28.1 | 71.1 | .0411 |
| " | 200 | 37.4 | 64.5 | .0496 |
| " | 215 | 49.3 | 60.0 | .0609 |
| III | 175 | 23.2 | 70.0 | .0365 |
| " | 185 | 33.6 | 73.5 | .0555 |
| " | 200 | 50.7 | 66.4 | .0756 |
| " | 215 | 56.3 | 60.1 | .0760 |
| IV | 175 | 22.6 | 74.4 | .0398 |
| " | 185 | 33.2 | 72.6 | .0566 |
| " | 200 | 52.1 | 61.9 | .0764 |
| " | 215 | 57.2 | 54.1 | .0733 |

From the foregoing results it can be seen that the optimum reaction temperature for the most rapid production of diisopropyl ether by dehydration of isopropanol with each of the four catalytic materials noted above appears to be substantially 200° C or slightly higher, the maximum rates ranging from substantially 0.060 to 0.075 grams mols per hour per gram of catalyst at the LHSV of substantially 10 with these catalyst materials. The significance of this can be appreciated by a comparison with the maximum practicable rate that can be achieved using "Dowex 50WX8" (trademark) as the catalyst under corresponding conditions, viz: LHSV substantially 10, pressure 1600 psig (110 atm.), temperature 150° C; this rate has been found to be substantially 0.043 gram mols per hour per gram of catalyst, which is at least 25% below the optima obtainable with the Montmorillonite clays. (Dowex 50WX8 is a commercial ion exchange resin material in the acid form, containing sulfonic acid groups as an apparently critical ingredient for its catalytic activity in dehydration of isopropanol.) The temperature of substantially 150° C is the practicable maximum at which this catalyst material can be used, as well as the temperature of optimum efficiency, as the material starts to desulfonate above 150° C, thereby losing its catalytic activity and also causing corrosion problems. Thus the greater thermal stability of the Montmorillonite catalysts permits achievement of rates of production from about 35 to 65% higher than the best that can be obtained practicably with the best practicable catalysts heretofore used in these reactions for diisopropyl ether production. Similar ion exchange resin catalysts made by other producers, e.g., "AGC-243" (trademark) and "Amberlyst A15" (trademark), suffer the same thermal instability above 150° C and are therefore inadequate in comparison to the Montmorillonite catalysts.

It can also be pointed out that comparisons with other acidic mineral materials, e.g., of the Lewis acid type, indicate that, even though they possess the thermal stability for utilization at temperatures of 200° C and higher, such materials have not been found suitable nor adequate as substitutes for the acid treated Montmorillonite clays used in the present invention for partial dehydration of isopropanol to diisopropyl ether. An example of such material which has been tried and found inadequate, in comparison with an acid treated Montmorillonite clay under comparable conditions of temperature, pressure, and flow rate, is "Linde Type 13X Molecular Sieves" (having a unit cell formula of $Na_{86}[(AlO_2)_{86}(SiO_2)_{106}] \cdot 276H_2O$ and an adsorption/exclusion threshold of substantially 10 Angstroms, sold by Linde Division, Union Carbide Company); acidity of the commercial material was assured by a succession of three soakings in warm normal sulfuric acid solution followed by washing with sufficient demineralized water to remove free acid. Another example of such material which has been found inadequate is "Silica Alumina Catalyst, Grade 979" sold by W. R. Grace & Company. This is a commercial extruded material of low density and high acidity, porosity, and surface area. Both the regular commercial form of this material and a modified form made by soaking the commercial material in oleum for 60 hours at room temperature and for a further 4 hours at 80° C, then washing with sufficient demineralised water to remove free acid, were tried under comparable conditions of temperature, pressure and flow rate, and found inadequate in comparison with acid treated Montmorillonite clay.

EXAMPLE 2

This example illustrates the preparation of diisopropyl ether by the partial dehydration of isopropanol in the presence of propylene with the simultaneous alcoholysis of propylene by isopropanol. The reactions were carried out in the same apparatus previously described for Example 1, with both isopropanol and propylene being pumped simultaneously and continuously to the reactor, at substantially equimolar rates. From chromatographic analysis of the product stream it was calculated that the actual molar ratio of isopropanol/propylene fed was 1.02. The temperature in the reactor was maintained at substantially 175° C and the pressure therein at substantially 750 psig (52 atm.), throughout the duration of the run, which was approximately 8 hours. A mixture of "KSF" Montmorillonite clay powder, dispersed on inert medium fibre asbestos in a weight ratio of 70/30, was packed into the reactor as the catalyst, and the rate of flow of the feeds over the catalyst, in the relative molar ratio previously indicated, produced a liquid hourly space velocity (LHSV) of 1.88. Chromatographic analysis of the effluent from the reactor, giving the proportions of diisopropyl ether, water, unreacted isopropanol, and unreacted propylene therein, established that 48.2% of the isopropanol feed was converted to diisopropyl ether (the remaining 51.8% of it being recoverable for recycling) and 7.6% of the propylene likewise was converted to diisopropyl ether by reaction with some of the foregoing converted isopropanol, (the remaining 92.4% of the propylene feed likewise being recoverable for recycling.). Thus the yield of diisopropyl ether in the single pass through the reactor, based on the $C_3$ hydrocarbon equivalent in the feed, was 28.2%. In view of the fact that, in the presence of an acidic material, isopropanol can dehydrate to produce water and free propylene, it could not be foreseen that acidic catalysis to promote the partial dehydration of isopropanol to diisopropyl ether could also so effectively simultaneously promote the alcoholysis of free propylene by some of the isopropanol to provide a net consumption of propylene instead of production of propylene as a by-product.

With regard to the foregoing Example 2, it can be pointed out that in attempted alcoholysis of propylene with isopropanol simultaneously with the partial dehydration of additional isopropanol, in presence of each of the other acidic mineral materials referred to above instead of the "KSF"Montmorillonite, but under otherwise comparable conditions of temperature, pressure, reactant feed ratios, and flow rate, no positive conversion of propylene to diisopropyl ether could be achieved and in contrast, a net conversion of isopropanol to free propylene occurred, producing a greater effluent thereof from the reactor than was present in the feed. For example, using "Linde Type 13X Molecular Sieves" acid treated as previously described, a feed of substantially equimolar isopropanol/propylene mixture gave an effluent containing propylene in a proportion of 109.5% of the amount of propylene in the feed, under reaction conditions otherwise substantially as described in Example 2. Others of the acid mineral materials referred to hereinbefore gave propylene effluents between about 4 and 40% greater than the propylene feeds, showing net conversion of isopropanol to propylene rather than alcoholysis of propylene to diisopropyl ether.

EXAMPLE 3

This example again illustrates the preparation of diisopropyl ether by the partial dehydration of isopropanol in the presence of propylene, this time over a range of temperatures and with the variety of different Montmorillonite catalysts previously indicated in Example 1. A pressure of substantially 1600 psig (110 atm.) was used for the runs, with feed rates providing an LHSV of substantially 10, in the same apparatus described in Example 1. A molar ratio of approximately 1:1 for the isopropanol:propylene feeds was attempted, but some variations therein did occur and must be considered to have influenced the results to a minor extent. In the series of runs as aforesaid, following the procedure used in Example 2, the diisopropyl ether (DIPE) production rates achieved, with the various catalysts identified in Example 1, at the indicated temperatures, expressed in gram mols per hour per gram of dry active catalyst ingredient, are shown in Table III.

TABLE III

| Catalyst | DIPE Production Rate (gM/hr/g Cat.) at: | | | |
|---|---|---|---|---|
| Type | 175° C | 185° C | 200° C | 210° C |
| I | .0181 | .0218 | .0388 | N.D.* |
| II | .0191 | .0221 | .0366 | .0341 |
| III | .0281 | .0331 | .0529 | .0565 |
| IV | .0220 | .0321 | .0551 | .0450 |

*Not Determined

The conversion of free propylene to diisopropyl ether by alcoholysis with isopropanol, as illustrated in Examples 2 and 3, is found to vary in relation to a number of parameters, including temperature, pressure, ratio of free propylene to isopropanol in the feed, and catalyst contact time (which is inversely proportional to the liquid hourly space velocity), as well as the activity of the particular catalyst used, which activity may alter with time for any particular catalyst.

The specific quantitative relationships between the parameters have not all been ascertained for all of the individual catalysts disclosed for the present invention, there being considerable complexity in the interrelationships making them difficult to determine. However, it can be indicated that, in the presence of the catalysts disclosed for the present invention, increasing temperatures of reaction increase the rate of conversion of isopropanol to reaction products, but because of the variety of reactions that do occur, the rate of production of diisopropyl ether does not increase continuously with increasing temperature; it appears that the rate of dehydration of isopropanol to propylene increases at a significantly faster rate with increasing temperature than does the rate of partial dehydration of isopropanol to diisopropyl ether. Because of this, the selectivity of the dehydration of isopropanol to produce diisopropyl ether appears to have an optimum temperature which depends upon the individual catalyst; because this selectivity decreases with increasing temperature at temperatures above the optimum, the actual overall rate of production is a more significant measure of the efficiency of a catalyst and operating parameters than is the rate of conversion of isopropanol or the selectively. It is for this reason that the diisopropyl ether production rates are given, in Examples 1 and 3, to illustrate the superior efficiency of the paticular catalysts in the present invention. The pressure under which the reactions are catalyzed does not have a large effect on the rate of diisopropyl ether production, inasmuch as the temperatures used in the claimed invention are above the critical temperatures of some of the other components in the reaction. Pressures under 500 psig (35 atm.) have been found to be operative, providing that a liquid phase is maintained, and pressures over 1600 psig (110 atm.) also have been found operative but not significantly advantageous over the lower operative pressures. It is thus convenient to carry out the invention under pressures in the range from 500 psig (35 atm.) to 1000 psig (69 atm.). When free propylene is in the feed, the propylene appears to occupy some active sites on the catalyst, thus reducing the number of sites available for catalyzing the partial dehydration of isopropanol to diisopropyl ether. The proportion of the active sites occupied by propylene will vary with its concentration in the feed, hence the higher concentrations of propylene in the feed tend to lower the rate of production of diisopropyl ether. Thus excess propylene in the feed does not tend to improve the ether production rate, and propylene/isopropanol ratios of less than stoichiometric are preferred. The time that the reactants are in contact with the catalyst does not have to be long, and liquid hourly space velocities (LHSV) as high as 50 have been found to be highly satisfactory; these provide a contact time near one minute. An LHSV as low as 0.5 also has been found to be operable (providing a contact time of two hours), but higher values are generally preferred for increased operating efficiency, with LHSV values from 5 to 25 being preferred. Although the catalysts used in the invention are substantially stable at the temperatures which are suitable for this invention, there may be some slight decrease in catalyst activity in time if operating temperatures above 215° C are used. Some regeneration of catalyst can be achieved by soaking it with sulfuric acid.

It can be appreciated from the disclosure above that acidic, sulfuric acid treated, Montmorillonite clay can be classed as an effective catalyst for the alcoholysis to ether, with isopropanol, of the olefinic hydrocarbon propylene; it has also been found that such Montmorillonite clays may also act as catalysts for the alcoholysis of other olefins, specifically tertiary olefins, with other alcohols to form ethers, in a manner apparently like the action of acidic ion exchange resins which catalyze such alcoholysis, as previously disclosed in the art. However, in such alcoholysis reactions the Montmorillonite clays are inferior, being less effective and less efficient in ether production than the previously used acidic ion exchange resins, and it is therefore all the more unexpected that the acidic Montmorillonite clays are more efficient as catalysts for the process of the present invention, for the preparation of diisopropyl ether, than are acidic ion exchange resins. The utility of the acidic Montmorillonite clays as catalysts for the alcoholysis of tertiary olefins, as referred to above, is not included in the invention claimed herein.

It can also be pointed out that the effectiveness of the catalysts for the process claimed herein also applies to certain other similar reactions. Thus the catalysts can be used to convert ethanol to diethyl ether by dehydration, with practically no side reaction forming ethylene; temperatures appropriate for such etherification reaction are somewhat higher than those appropriate for conversion of isopropanol to diisopropyl ether. Likewise the mixed ether ethyl isopropyl ether can be produced from ethanol and propylene in presence of the catalysts used in the present invention. Similarly normal propyl alcohol can be converted to di-n-propyl ether in presence of the catalysts used in the present invention, and a mixture of normal propanol and propylene can be reacted to form n-propyl isopropyl ether in presence of these catalysts.

Numerous modifications of the specific expedients described herein can be made without departing from the scope of the invention which is defined in the following claims.

What is claimed is:

1. A process for the preparation of diisopropyl ether which comprises continuously feeding isopropanol, and optionally propylene, in the liquid phase under pressure into a reactor in which the feed material comes into effective contact with a solid catalyst, continuously withdrawing a mixture of reaction products and unreacted isopropanol and propylene from the reactor, and recovering diisopropyl ether from the mixture, said solid catalyst comprising acidic, sulfuric acid treated, Montmorilonite clay containing sufficient residual acidity to impart a pH below 4 thereto, said reactor being heated to maintain a temperature in the reactor in the range from substantially 120° C to substantially 250° C.

2. A process for the preparation of diisopropyl ether which comprises continuously feeding isopropanol, and optionally propylene, in the liquid phase under pressure into an elongated reactor containing a solid catalyst, continuously withdrawing the resulting mixture of reaction products and unreacted isopropanol and propylene from the reactor at a point remote from the point of introduction of the reactants, and recovering diisopropyl ether from the mixture, said solid catalyst comprising acidic, sulfuric acid treated, Montmorillonite clay containing sufficient residual acidity to impart a pH below 4 thereto, and said reactor being heated to maintain a temperature in the reactor in the range from substantially 120° C to substantially 250° C.

3. A process as claimed in claim 1 in which the pressure in the reactor is maintained in the range from 500 to 1000 psig (35 to 69 atmospheres).

4. A process as claimed in claim 2, in which isopropanol alone is continuously fed into a tubular reactor containing finely divided Montmorillonite clay dispersed on inert carrier, at a liquid hourly spaced velocity in the range from 0.5 to 50, with the temperature of reaction in the reactor being maintained in the range from 175° to 225° C.

5. A process as claimed in claim 2 in which a mixture of isopropanol and propylene, in molar proportions up to substantially one mole propylene per mole of isopropanol, is fed to the reactor in liquid phase, at a liquid hourly space velocity in the range from 0.5 to 50 while the temperature in the reactor is maintained in the range from 175° to 225° C.

6. A process as claimed in claim 5 in which the liquid hourly space velocity is in the range from 5 to 25.

7. A process as claimed in claim 5 in which the pressure in the reactor is maintained in the range from 500 to 1600 psig (35 to 110 atmospheres).

* * * * *